(12) United States Patent
Sato et al.

(10) Patent No.: US 10,302,589 B2
(45) Date of Patent: May 28, 2019

(54) GAS SENSOR, ELECTRICALLY CONDUCTIVE OXIDE SINTERED BODY, AND WIRING BOARD

(71) Applicant: NGK SPARK PLUG CO., LTD., Nagoya-shi, Aichi (JP)

(72) Inventors: Mina Sato, Singapore (SG); Yoshinobu Hirose, Nagoya (JP); Akira Seike, Komaki (JP); Hisashi Kozuka, Ichinomiya (JP); Yasuyuki Okimura, Inuyama (JP); Kazushige Ohbayashi, Nagoya (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 0 days.

(21) Appl. No.: 15/670,467

(22) Filed: Aug. 7, 2017

(65) Prior Publication Data

US 2018/0045673 A1 Feb. 15, 2018

(30) Foreign Application Priority Data

Aug. 12, 2016 (JP) .................. 2016-158401

(51) Int. Cl.
*G01N 27/12* (2006.01)
*G01N 27/30* (2006.01)
(Continued)

(52) U.S. Cl.
CPC ......... *G01N 27/4073* (2013.01); *C01G 53/70* (2013.01); *G01N 27/301* (2013.01);
(Continued)

(58) Field of Classification Search
CPC .... G01N 27/125; G01N 27/30; G01N 27/304; G01N 27/406; G01N 27/407;
(Continued)

(56) References Cited

U.S. PATENT DOCUMENTS

| | | | |
|---|---|---|---|
| 6,054,403 A | 4/2000 | Kawase et al. | |
| 2009/0013761 A1 * | 1/2009 | Chou .................. | G01N 27/407 73/31.05 |

(Continued)

FOREIGN PATENT DOCUMENTS

| | | | |
|---|---|---|---|
| CN | 102201579 A | 9/2011 | |
| DE | 2341256 A1 * | 2/1975 | ........... G01N 27/333 |

(Continued)

OTHER PUBLICATIONS

DE2341256A1, Steiner Rolf Dr; English equivalent of the Abstract (Year: 1975).*

(Continued)

*Primary Examiner* — Susan D Leong
(74) *Attorney, Agent, or Firm* — Sughrue Mion, PLLC (57) ABSTRACT

A gas sensor including a conductive oxide sintered body, the sintered body including a crystal phase having a perovskite-type oxide crystal structure represented by a compositional formula: $RE_aCu_bFe_cNi_dO_x$ wherein RE represents a rare earth element, wherein the following conditions: $a+b+c+d=1$ and $1.25 \leq x \leq 1.75$ are satisfied, and wherein a, b, c, and d satisfy the following conditions: $0.375 \leq a \leq 0.524$; $0.050 < b \leq 0.200$; $0.025 \leq c \leq 0.250$; and $0.150 \leq d \leq 0.350$. Also disclosed is a conductive oxide sintered body, a wiring board including a conductor layer formed of the conductive oxide sintered body and a gas sensor including an electrode formed of the conductive oxide sintered body.

7 Claims, 7 Drawing Sheets

(51) Int. Cl.
*C01G 53/00* (2006.01)
*G01N 27/407* (2006.01)
*H05K 1/09* (2006.01)
*H05K 3/12* (2006.01)

(52) U.S. Cl.
CPC ........... *G01N 27/4076* (2013.01); *H05K 1/09* (2013.01); *C01P 2002/34* (2013.01); *C01P 2002/50* (2013.01); *C01P 2006/40* (2013.01); *H05K 1/092* (2013.01); *H05K 3/1291* (2013.01); *H05K 2201/0326* (2013.01)

(58) Field of Classification Search
CPC ........... G01N 27/4071; G01N 27/4073; G01N 27/4074; G01N 27/4075; G01N 27/4076
See application file for complete search history.

(56) References Cited

U.S. PATENT DOCUMENTS

2011/0236789 A1   9/2011   Namba et al.
2015/0099142 A1   4/2015   Kozuka et al.
2018/0330843 A1   11/2018   Kozuka et al.

FOREIGN PATENT DOCUMENTS

| JP | 11-116334 A | 4/1999 |
| JP | 2002-87882 A | 3/2002 |
| JP | 2012-169240 A | 9/2012 |
| JP | 2012-198990 A | 10/2012 |
| JP | 2016-158401 A | 9/2016 |
| WO | 2013/150779 A1 | 10/2013 |
| WO | 2016/098309 A1 | 6/2016 |

OTHER PUBLICATIONS

Tai, et al., "Structure and electrical properties of $La_{1-x}Sr_xCo_{1-y}Fe_yO_3$. Part 2. The system $La_{1-x}Sr_xCo_{0.2}Fe_{0.8}O_3$", Solid State Ionics, 1995, vol. 76, pp. 273-283.

Communication dated Dec. 19, 2018 issued by the State Intellectual Property Office of P.R. China in counterpart Chinese Application No. 201710686947.6.

* cited by examiner

GAS SENSOR, ELECTRICALLY CONDUCTIVE OXIDE SINTERED BODY, AND WIRING BOARD

BACKGROUND OF THE INVENTION

1. Field of the Invention

The present invention relates to a gas sensor, an electrically conductive oxide sintered body for use in a gas sensor, an electrically conductive oxide sintered body, and a wiring board.

2. Description of the Related Art

Generally, ceramic electronic devices have a ceramic substrate and electrodes disposed on the substrate, and such electrodes are formed of a metallic material. Such ceramic electronic devices include, for example, multi-layer ceramic capacitors equipped with an Ni electrode, a Pd electrode, or a Pt electrode; low temperature co-fired ceramic (LTCC) parts equipped with an Ag electrode, a Cu electrode, or an Ag—Pd electrode; piezo-actuators having a Pd electrode; semiconductor packages employing a W electrode; and spark plugs having an Ir electrode or a Pt electrode.

Among the above metal elements, Ni, Cu, and W must be fired with a ceramic substrate in a controlled atmosphere. Thus, difficulty is encountered in attaining characteristics intrinsic to the target ceramic substrate, and production costs rise, which is problematic. In the case of Ag, which has a low melting point (962° C.), the material of the ceramic substrate is limited. In addition, when the substrate is fired at a low temperature, the characteristics of the ceramic substrate may be impaired. Noble metals such as Pd, Ir, and Pt are expensive, making application of such materials to large area electrodes difficult.

Patent Document 1 discloses, as an oxide electrode material, a lanthanum cobalt oxide having a negative temperature characteristic such that the resistance thereof is high at ambient temperature and lowers with rising temperatures. Patent Document 2 discloses a lanthanum cobalt oxide having a negative temperature characteristic such that the resistance thereof is high at room temperature and the absolute value of its B constant is large at a high temperature. However, the conductive oxides disclosed in Patent Documents 1 and 2 exhibit high resistivity, i.e., poor conductivity, at room temperature.

As described above, conventional oxides have a conductivity which is considerably lower than that of metallic materials, and a large absolute B constant value (temperature coefficient). Therefore, difficulty is encountered in replacing a metal electrode with a ceramic electrode. Meanwhile, ruthenium oxides (e.g., $RuO_2$ and $SrRuO_3$) are known to have high conductivity, but are problematically expensive. Under such circumstances, the present applicant discloses in Patent Document 3 an oxide sintered body which has a high conductivity and a small absolute B constant value (temperature coefficient) and which is suited for a conductive material. Also, Non-Patent Document 1 discloses various types of perovskite oxides. Patent Documents 4 and 5 disclose lanthanum-nickel-copper-iron perovskite oxides ((La, Ni)(Cu, Fe)$O_3$). The oxides disclosed in Patent Documents 4 and 5 are used as, for example, an electrode oxide material for solid oxide fuel cells.

PATENT DOCUMENTS

Patent Document 1: Japanese Patent Application Laid-Open (kokai) No. 1999-116334
Patent Document 2: Japanese Patent Application Laid-Open (kokai) No. 2002-087882
Patent Document 3: WO 2013/150779
Patent Document 4: Japanese Patent Application Laid-Open (kokai) No. 2012-169240
Patent Document 5: Japanese Patent Application Laid-Open (kokai) No. 2012-198990

NON-PATENT DOCUMENTS

Non-Patent Document 1: Solid State Ionics, 76(1995), 273

3. Problems to be Solved by the Invention

However, in some cases, conventional conductive oxides fail to exhibit a high conductivity at low temperatures (e.g., <600° C.), although they exhibit a high conductivity at high temperatures (e.g., ≥600° C.). Thus, there is demand for a conductive oxide sintered body which also exhibits a high conductivity at lower temperatures. Meanwhile, when such a conductive oxide sintered body is employed as a gas sensor electrode formed on a sintered oxide substrate, the gas sensor is also operational at room temperature. Therefore, the conductive oxide sintered body preferably exhibits a high conductivity at room temperature (hereinafter also referred to as room temperature conductivity). Under such circumstances, there is also demand for a conductive oxide sintered body which attains a high conductivity at room temperature.

SUMMARY OF THE INVENTION

The present invention has been made so as to solve the above-described problems. It is therefore an object of the present invention to provide a gas sensor including a conductive oxide sintered body, a conductive oxide sintered body, a wiring board including a conductor layer formed of the conductive oxide sintered body, and a gas sensor including an electrode formed of the conductive oxide sintered body, which conductive oxide sintered body attains high conductivity at room temperature.

The above objects of the invention have been achieved by providing, in a first aspect (1) a gas sensor comprising a conductive oxide sintered body, the conductive oxide sintered body including a crystal phase having a perovskite-type oxide crystal structure represented by a compositional formula: $RE_aCu_bFe_cNi_dO_x$ wherein RE represents a rare earth element, wherein the following conditions: a+b+c+d=1 and 1.25≤x≤1.75 are satisfied, and wherein a, b, c, and d satisfy the following conditions:

$0.375 \leq a \leq 0.524$;

$0.050 < b \leq 0.200$;

$0.025 \leq c \leq 0.250$; and $0.150 \leq d \leq 0.350$.

According to the gas sensor (1) above, the conductive oxide sintered body has a room temperature conductivity of 200 S/cm or higher. As used herein, the term "room temperature conductivity" refers to an electrical conductivity measured at 25° C.

In a preferred embodiment (2) of the gas sensor (1) above, the rare earth element RE is La.

According to the gas sensor (2) above, the room temperature conductivity of the conductive oxide sintered body can be further enhanced.

In another preferred embodiment (3) of the gas sensor (2) above, a, b, c, and d satisfy the following conditions:

$0.412 \leq a \leq 0.524$;

$0.060 \leq b \leq 0.200$;

$0.025 \leq c \leq 0.200$; and $0.200 \leq d \leq 0.350$.

According to the gas sensor (3) above, the conductive oxide sintered body has a room temperature conductivity of 500 S/cm or higher.

In yet another preferred embodiment (4) of the gas sensors (2) or (3) above, b is smaller than c.

According to the gas sensor (4) above, the amount of Cu (in terms of atom %) is smaller than that of Fe. Thus, a conductive oxide sintered body can be provided having a lower thermal expansion coefficient, as compared with the case in which the amount of Cu is equal to or higher than that of Fe.

In a second aspect (5), the present invention provides a conductive oxide sintered body including a crystal phase having a perovskite-type oxide crystal structure represented by a compositional formula: $RE_aCu_bFe_cNi_dO_x$ wherein RE represents a rare earth element, wherein the following conditions: $a+b+c+d=1$, $1.25 \leq x \leq 1.75$, and $a<(b+c+d)$ are satisfied, and wherein a, b, c, and d satisfy the following conditions:

$0.412 \leq a < 0.500$;

$0.060 < b \leq 0.200$;

$0.025 \leq c \leq 0.200$; and $0.150 \leq d \leq 0.350$.

According to (5) above, the conductive oxide sintered body has a room temperature conductivity of 500 S/cm or higher, even when deficient in a rare earth element RE (i.e., $a<(b+c+d)$).

In a third aspect (6), the present invention provides a wiring board comprising a ceramic substrate, and a conductor layer formed of the conductive oxide sintered body as defined in (5) above and disposed on a surface of the ceramic substrate.

According to (6) above, the wiring board has a conductor layer exhibiting a room temperature conductivity of 500 S/cm or higher, even when deficient in a rare earth element RE (i.e., $a<(b+c+d)$).

In a fourth aspect (7), the present invention provides a gas sensor comprising an electrode formed of the conductive oxide sintered body as defined in (5) above.

According to (7) above, the gas sensor has an electrode exhibiting a room temperature conductivity of 200 S/cm or higher.

The gas sensor (7) above may be an oxygen sensor having an electrode exhibiting a room temperature conductivity of 200 S/cm or higher.

In the gas sensor (7) above, the electrode may be a reference electrode having a reference electrode exhibiting a room temperature conductivity of 200 S/cm or higher.

The present invention can be realized as various embodiments. Such embodiments include, for example, a production method for a conductive oxide sintered body; various devices and materials each employing the conductive oxide sintered body, such as electrodes, thermoelectric materials, heater materials, and temperature-sensing elements; and production methods therefor.

DESCRIPTION OF REFERENCE NUMERALS

Reference numerals used to identify various features in the drawings include the following.

20: metallic shell
20a: bent portion
20b: step portion
20c: flange portion
20d: male screw portion
29: gasket
31: powder charged portion
32: insulating member
33: metal ring
34: separator
35: passage hole
36: grommet
37: filter
38: protecting outer tube
39: second vent hole
40: outer tube
41: first vent hole
60: lead wire
62: protector
70: connection terminal
100: gas sensor element
110: substrate
120: outside electrode
130: reference electrode
140: flange portion
300: gas sensor

DETAILED DESCRIPTION OF THE PREFERRED EMBODIMENTS

The present invention will next be described in greater detail by reference to the drawings. However, the present invention should not be construed as being limited thereto.

A. Conductive Oxide Sintered Body

An embodiment of the conductive oxide sintered body of the present invention includes a crystal phase having a perovskite-type oxide crystal structure represented by the following compositional formula (1).

$$RE_aCu_bFe_cNi_dO_x \qquad (1)$$

In formula (1), RE represents a rare earth element, and the following conditions: a+b+c+d=1 and 1.25≤x≤1.75 are satisfied.

Also, the coefficients a, b, c, and d satisfy the following conditions:

$$0.375 \le a \le 0.524 \qquad (2a);$$

$$0.050 < b \le 0.200 \qquad (2b);$$

$$0.025 \le c \le 0.250 \qquad (2c); \text{ and}$$

$$0.150 \le d \le 0.350 \qquad (2d).$$

When the above relationships (2a) to (2d) are satisfied, a room temperature conductivity of 200 S/cm or higher can be attained. In this case, a conductive oxide sintered body can be provided for use in a gas sensor, which sintered body is suited for an electrode of the gas sensor. As used herein, the concept "room temperature conductivity" refers to an electrical conductivity measured at 25° C.

When the conductive oxide sintered body satisfies the above compositional relationships (2a) to (2d), the firing temperature for production thereof may be adjusted to 1,100° C. Thus, in the case where a conductive oxide sintered body is formed by secondary firing of a paste of the corresponding conductive oxide sintered body applied onto a generally employed oxide substrate (e.g., aluminum oxide or zirconium oxide), reaction at the interface between the substrate and the conductive oxide sintered body can be suppressed.

In the case where the conductive oxide sintered body having the above composition is completely formed of a perovskite phase, the coefficient "x" with respect to O (oxygen) is theoretically 1.50. However, the oxygen content may deviate from the stoichiometric composition in response to the metal element content of the perovskite-type oxide, or the temperature and type of ambient. Thus, the range of x is defined as a typical range: 1.25≤x≤1.75 in formula (1).

So long as the conductive oxide sintered body according to the embodiment of the present invention includes a perovskite phase having the above composition, another oxide may also be present. When an X-ray diffraction peak attributed to an $RE.MO_3$ (wherein M is Cu, Fe, or Ni) oxide is detected by XRD (X-ray diffraction) in the conductive oxide sintered body, the conductive oxide sintered body is determined to contain a perovskite phase. However, the conductive oxide sintered body preferably includes a perovskite phase having the above composition in an amount of 50 mass % or more.

Notably, the conductive oxide sintered body according to the embodiment of the present invention may further contain a very small amount of an alkaline earth metal element, so long as the conductivity thereof is not impaired. However, preferably, the conductive oxide sintered body contains substantially no alkaline earth metal element. Under the above conditions, even when the conductive oxide sintered body is exposed to an atmosphere at room temperature (25° C.) to about 900° C., absorption and release of oxygen are impeded, whereby variation in weight of the sintered body is minimized. As a result, an oxide sintered body which is suitable as a conductive material for use under high-temperature conditions can be produced. As used herein, the concept "substantially containing no alkaline earth metal element" refers to an alkaline earth metal element content of 0.3% (weight basis) or lower, which is determined through elemental analysis via ICP (inductively coupled plasma) emission spectrometry. The ICP emission spectrometry is carried out according to JIS K0116 (2014). Analytical samples are preliminarily treated through the hydrochloric acid dissolution technique. In the case where a conductive oxide sintered body containing an alkaline earth metal element such as Sr is employed as an electrode of a gas sensor (e.g., an oxygen sensor), the alkaline earth metal element diffuses into the gas sensor substrate (e.g., yttria-stabilized zirconia) during long-term use under high temperature actual working conditions. In such a case, impairment in performance of the electrode due to diffusion of the alkaline earth metal element, or performance of the gas sensor (e.g., reduction in impedance) may occur. Thus, preferably, the conductive oxide sintered body contains substantially no alkaline earth metal element.

The rare earth element RE may include, among rare earth elements, at least one element selected from among La (lanthanum), Ce (cerium), Pr (praseodymium), Nd (neodymium), Pm (prometium), Sm (samarium), etc. The rare earth element RE preferably includes at least one element selected from La, Pr, and Nd.

Particularly, when the rare earth element RE consists of La, a conductive oxide sintered body having higher room temperature conductivity can be produced, which is preferred. When the rare earth element RE consists of La, the absolute value of B constant (temperature coefficient) is preferably lowered. Thus, a conductive oxide sintered body can be provided which is more suited as an electrode of a gas sensor.

Notably, the aforementioned coefficients a, b, c, and d more preferably satisfy the following conditions:

$$0.412 \le a \le 0.524 \qquad (3a);$$

$$0.060 \le b \le 0.200 \qquad (3b);$$

$$0.025 \le c \le 0.200 \qquad (3c); \text{ and}$$

$$0.200 \le d \le 0.350 \qquad (3d).$$

When the coefficients a, b, c, and d satisfy the above conditions, a room temperature conductivity of 500 S/cm or higher can be attained. Thus, a conductive oxide sintered body can be provided which is further suited as an electrode of a gas sensor.

Furthermore, the coefficient with Cu "b" is preferably smaller than that with Fe "c." When the coefficient b is smaller than the coefficient c, the amount of Cu in the conductive oxide sintered body (in terms in atom %) is smaller than the amount of Fe. Thus, the thermal expansion coefficient can be reduced, as compared with the case in which the amount of Cu is equal to or higher than that of Fe. Specifically, the thermal expansion coefficient can be modified to the level of the thermal expansion coefficient of an oxide substrate (e.g., aluminum oxide or zirconia (more specifically, yttria-stabilized zirconia)) generally employed as a gas sensor substrate. Thus, in the case where a conductive oxide sintered body is formed by secondary firing of a paste of the corresponding conductive oxide sintered body applied onto such a substrate, generation of cracks and the like can be prevented, which would otherwise be caused by the difference in thermal expansion coefficient between the substrate and the conductive oxide sintered body. Generally, a gas sensor is actually operated under frequent rapid-heating/cooling cycle conditions. Thus, in order to prevent crack generation and removal of the conductive oxide sintered body from the substrate, the difference in thermal expansion coefficient between the substrate and the conductive oxide sintered body is preferably small.

Formula (1) above may satisfy the following conditions: a+b+c+d=1, 1.25≤x≤1.75, and a<(b+c+d), and the coefficients a, b, c, and d satisfy the following conditions:

$$0.412 \leq a < 0.500 \quad (4a);$$

$$0.060 \leq b \leq 0.200 \quad (4b);$$

$$0.025 \leq c \leq 0.200 \quad (4c); \text{ and}$$

$$0.150 \leq d \leq 0.350 \quad (4d).$$

When the coefficients a, b, c, and d satisfy the above conditions, a room temperature conductivity of 500 S/cm or higher can be attained. Thus, in the case where a conductive oxide sintered body is formed by secondary firing of a paste of the corresponding conductive oxide sintered body applied onto an oxide substrate (e.g., aluminum oxide or zirconium oxide) generally employed as a substrate of a gas sensor, a high room temperature conductivity can be attained, even when a rare earth element RE becomes deficient relative to its stoichiometric amount (a<(b+c+d)) due to diffusion of the rare earth element RE in the conductive oxide sintered body. Therefore, when the coefficients a, b, c, and d satisfy the above conditions, a conductive oxide sintered body can be provided which is further suited as an electrode of a gas sensor. In addition, high room temperature conductivity can be attained, even when the rare earth element RE amount is reduced, whereby the production cost for a conductive oxide sintered body can be reduced.

The conductive oxide sintered body according to the embodiment of the present invention may be employed as a metallic electrode material substitute in other than a gas sensor electrode, such as electric wirings, conductive members, thermoelectric material, heater material, and temperature-sensing elements. In one specific example, a conductive member or a wiring board may be produced by forming, on the surface of a ceramic substrate, a conductor layer made of the conductive oxide sintered body.

Meanwhile, in some cases, a conductive oxide sintered body having a perovskite-type oxide crystal structure is employed as an electrode material of a solid oxide fuel cell. However, the conductive oxide sintered body employed in a solid oxide fuel cell is not always suited for that employed as an electrode material of a solid oxide fuel cell of a gas sensor. Since a solid oxide fuel cell is operated at 600° C. or higher (e.g., 700 to 1,000° C.), the conductive oxide sintered body used in the solid oxide fuel cell is generally formed of a material exhibiting a high conductivity at a relevant temperature. However, there are some cases in which the selected conductive oxide sintered body exhibits low conductivity at 600° C. or lower, or a considerable variation in conductivity with a change in temperature. Generally, a gas sensor is operated at relatively low temperature (room temperature to lower than 600° C.) or 200° C. or higher. Therefore, if a conductive oxide sintered body for use in a solid oxide fuel cell is applied to an electrode of a gas sensor, an accurate gas concentration determination may not be attained. Similarly, such a conductive oxide sintered body as employed in a solid oxide fuel cell may not be suited for a ceramic-made element which is operated at room temperature or higher, or at a temperature below zero or higher, or for use in a wiring board.

B. Method for Producing Conductive Oxide Sintered Body

Figure 1:
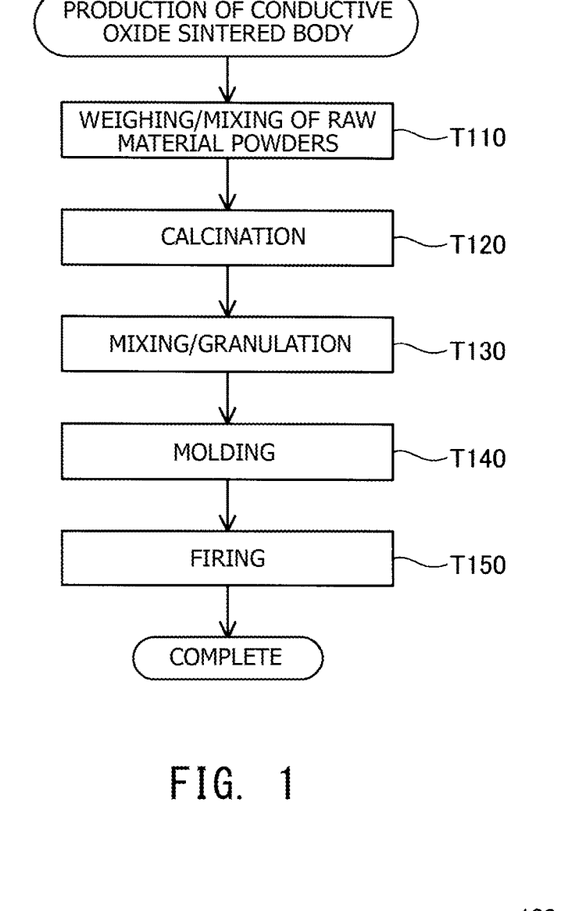
FIG. 1 is a flowchart illustrating a method of manufacturing an embodiment of the conductive oxide sintered body of the present invention.

FIG. 1 is a flowchart showing a method of manufacturing an embodiment of the conductive oxide sintered body of the present invention. In producing the conductive oxide sintered body, powders of raw materials are weighed and mixed (step T110). According to this embodiment, in step T110, raw materials in powder form are weighed, mixed under wet conditions, and dried, to thereby prepare a raw material mixture powder. Examples of powder form raw materials include $RE(OH)_3$, $CuO$, $Fe_2O_3$, and $NiO$. All these material powders preferably have a purity of 99% or higher. As an RE source, $RE_2O_3$ may be used instead of $RE(OH)_3$. However, use of $RE(OH)_3$ or no use of $RE_2O_3$ is preferred. The reason for this is that difficulty is encountered in precise mixing of $RE_2O_3$ (e.g., $La_2O_3$) due to water absorbability thereof, possibly causing a drop in conductivity and reproducibility.

Subsequently, the raw material mixture powder is calcined, to thereby form a calcined powder (step T120). Calcining may be performed in air at 700 to 1,200° C. for 1 to 5 hours.

Then, an appropriate amount of an organic binder is added to the calcined powder, and the mixture is granulated (step T130). In one mode of the granulation carried out in step T130, an appropriate amount of organic binder is added to the calcined powder, and the mixture is put into a resin pot with a dispersion medium (e.g., ethanol). The resultant mixture is mixed and pulverized by means of zirconia balls under wet conditions, to thereby yield a slurry. The thus-obtained slurry is dried at 80° C. for about 2 hours, and the dried product is granulated through a 250-μm mesh, to thereby yield a granulated powder.

Then, the thus-obtained granulated powder is molded (step T140). Molding may be performed by means of a press machine (molding pressure: 98 MPa).

Then, the obtained compact is fired at a firing temperature higher than the calcination temperature, to thereby yield a sintered conductive oxide body (step T150). In one mode of firing, the compact is fired in air for 1 to 5 hours at 1,000 to 1,550° C. The firing temperature is preferably about 1,100° C. If required, the surface of the conductive oxide sintered body may be polished after firing.

Notably, no substantial loss of metal elements in the material powder is observed in the production steps of the embodiment. As a result, the metal element proportions in the produced conductive oxide sintered body are substantially the same as those of the raw material powder obtained in mixing step T110.

Whether or not the conductive oxide sintered body has the aforementioned composition may be determined by ICP analysis of the relevant conductive oxide sintered body. In the analysis, a sample is dissolved in 50-vol % aqueous nitric acid. In the case where the level of the analytical target element of the sample is 1,000 ppm or higher, ICP-AES (ICP atomic emission spectroscopy) is employed, whereas in the case where the level is lower than 1,000 ppm, ICP-MS (ICP mass spectroscopy) is employed. ICP-AES may be performed by means of iCAP6000 (Thermo Fisher Scientific), and ICP-MS may be performed by means of iCAPQ (Thermo Fisher Scientific). ICP-MS analysis may be performed in the collision mode. In the analysis, a calibration curve is obtained using standard solutions, and each measurement is adjusted by reference to the calibration curve, to thereby obtain the compositional proportions in the conductive oxide sintered body.

C. Gas Sensor Element

Figure 2:
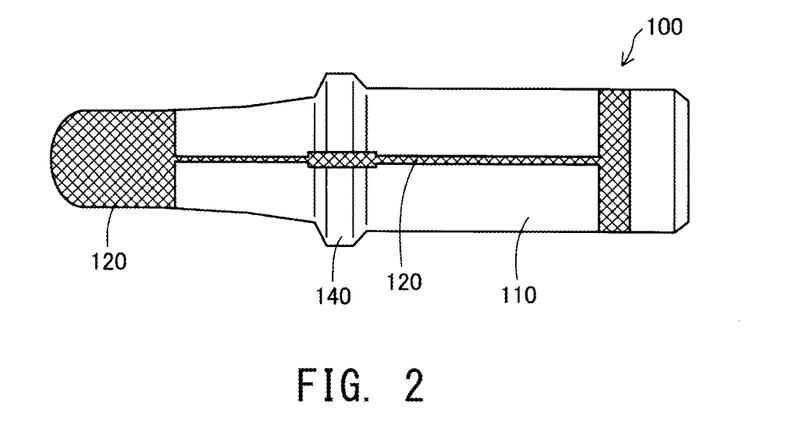
FIG. 2 is a front view of a gas sensor element employing the embodiment of the conductive oxide sintered body as an electrode material.
Figure 3:
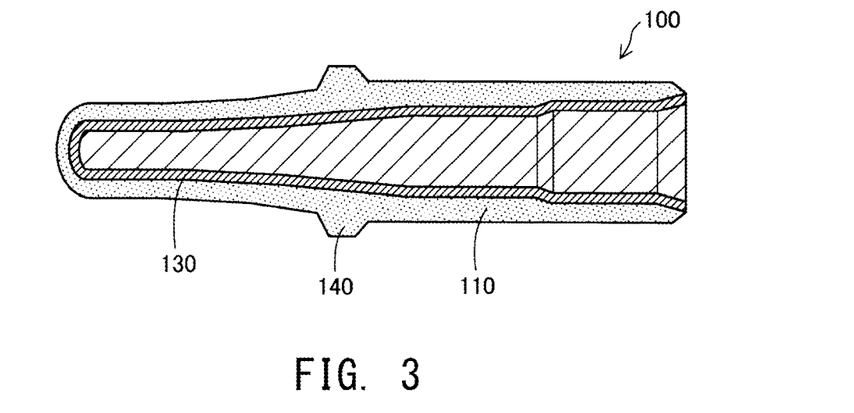
FIG. 3 is a sectional view of the gas sensor element shown in FIG. 2.

FIG. 2 is a front view of a gas sensor element 100 employing the embodiment of the conductive oxide sintered body as an electrode material. FIG. 3 is a sectional view of the gas sensor element 100 shown in FIG. 2. In the embodiment, the gas sensor element 100 is an oxygen sensor element. The gas sensor element 100 has an elongated shape extending along an axial line and includes a substrate 110 made of a ceramic material (solid electrolyte) having a shape of a bottomed tube; a noble metal outside electrode 120 formed on the outer surface of the substrate 110; and a standard electrode (reference electrode) 130 formed on the inner surface of the substrate 110.

The reference electrode 130 is a conductor layer formed of the conductive oxide sintered body of the aforementioned embodiment. In the gas sensor element 100 of the embodiment, the reference electrode 130 is provided on virtually the entire inner surface of the substrate 110. The reference electrode 130 which comes into contact with a reference gas (e.g., air) having a reference oxygen concentration for oxygen concentration detection. The length of the reference electrode 130 along the axial line direction may be appropriately modified in accordance with the size of the gas sensor element 100, but is typically 1 to 10 cm. The outside electrode 120 comes into contact with a measurement gas (e.g., exhaust gas).

The solid electrolyte forming the substrate 110 may be, for example, zirconium oxide ($ZrO_2$) to which yttrium oxide ($Y_2O_3$) has been added (i.e., yttria-stabilized zirconia (YSZ)). Alternatively, the gas element 100 may also be formed from a stabilized zirconia containing an oxide stabilizer selected from among calcium oxide (CaO), magnesium oxide (MgO), cerium oxide ($CeO_2$), aluminum oxide ($Al_2O_3$), and other oxides, or from any of other solid electrolytes. As used herein, the "stabilized zirconia" refers to a completely stabilized zirconia and a partially stabilized zirconia. Notably, a flange portion 140 protruding toward the radial direction is provided on the gas sensor element 100 (substrate 110) at an approximately middle position along the axial line such that the flange portion 140 completely covers the periphery of the substrate 110.

Figure 4:
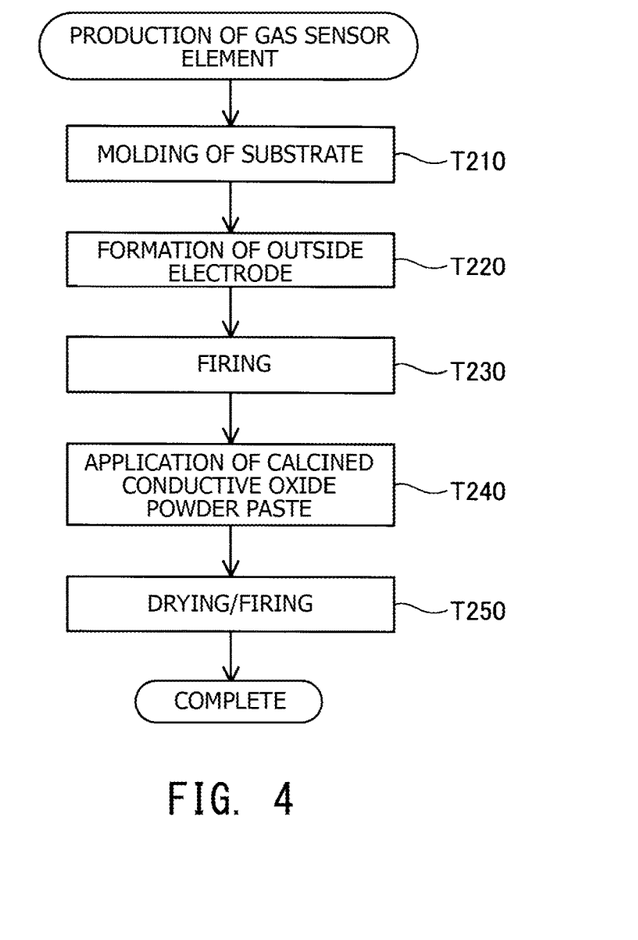
FIG. 4 is a flowchart showing a method of manufacturing a gas sensor element.

FIG. 4 is a flowchart showing a method of manufacturing the gas sensor element 100. In producing the gas sensor element 100, firstly, the substrate 110 is formed (step T210). Specifically, a material of the substrate 110 (e.g., yttria-stabilized zirconia powder) is press-molded, and the molded product is cut into a shape (tube) shown in FIG. 2 or 3, to thereby yield a green product (an unsintered molded product).

Subsequently, the outside electrode 120 is provided on the surface of the thus-obtained green product (step T220). The outside electrode 120 may be formed using a Pt paste or an Au paste through printing or dipping on the surface.

Then, the thus-obtained body having the outside electrode 120 formed on the green substrate is fired (step T230). The firing step may be performed in air at 1,250 to 1,600° C. for 1 to 5 hours. In this way, a sintered body (e.g., a yttria-stabilized zirconia sintered body) having the outside electrode 120 formed on the substrate can be produced.

Then, a paste of the calcined powder of the conductive oxide sintered body is applied onto the inner surface of the sintered body, to thereby form the reference electrode 130 (step T240). Next, specifically, the calcined powder of the conductive oxide sintered body formed in steps T110 and T120 shown in FIG. 1 is dissolved in a solvent such as terpineol or butyl carbitol with a binder such as ethylcellulose, to thereby prepare a paste. The paste is applied onto the inner surface of the sintered yttria-stabilized zirconia tube.

The zirconia tube in which the paste of the calcined powder of the conductive oxide has been applied onto the inner surface thereof is dried and fired, to thereby produce the gas sensor element 100 (step T250). The firing may be performed, for example, in air at 1,100° C. for 1 to 5 hours. Note that the aforementioned conditions of the production methods mentioned in relation to FIGS. 1 and 4 are given only for illustration. Thus, it should be noted that those skilled in the art can modify those conditions in accordance with use of the products and other factors.

D. Gas Sensor

Figure 5:
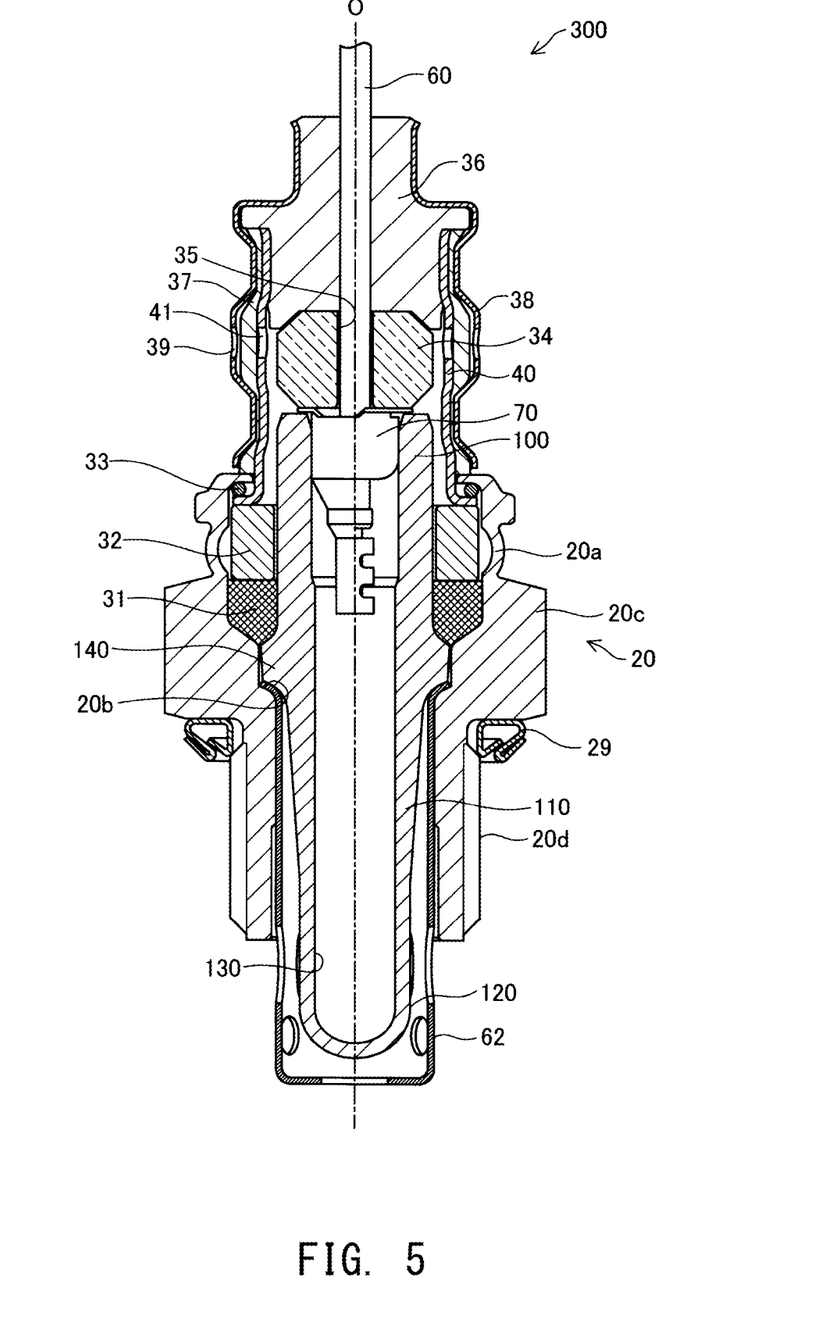
FIG. 5 is a sectional view of a gas sensor as an embodiment of the present invention.

FIG. 5 is a sectional view of the structure of an embodiment of a gas sensor 300 according to the present invention. The gas sensor 300 serves as, for example, an oxygen sensor for detecting the oxygen concentration of an exhaust gas from an internal combustion engine. The gas sensor 300 has an elongated shape extending along an axial line O. In the flowing description, the lower side of FIG. 5 will be referred to as a forward end side, and the upper side thereof will be referred to as a rear end side. Also, a direction which is orthogonal to the axial line O and is directed outward from the axial line O will be referred to as the "radial direction." The gas sensor 300 includes the aforementioned gas sensor element 100 of the above embodiment, a metallic shell 20, a protector 62, an outer tube 40, a protecting outer tube 38, and a lead wire 60 drawn from the reference electrode 130 of the gas sensor element 100.

The metallic shell 20 is a member formed of a metal (e.g., stainless steel) and surrounding the gas sensor element 100, and a forward end portion of the gas sensor element 100 projects from a forward end portion of the metallic shell 20. The metallic shell 20 has a step portion 20b provided on the inner surface thereof such that the inner diameter decreases toward the forward end. The metallic shell 20 has a polygonal flange portion 20c which is provided at a position near the center of the metallic shell 20 and projects radially outward. An attachment tool such as a hexagonal wrench is engaged with the polygonal flange portion 20c. Further, a male screw portion 20d is formed on the outer surface located on the forward end side of the flange portion 20c. The male screw portion 20d of the metallic shell 20 is attached to a screw hole of an exhaust pipe of, for example, an internal combustion engine, whereby the forward end of the gas sensor element 100 is disposed within the exhaust pipe. Thus, the oxygen concentration of the gas (exhaust gas) can be detected. Further, a gasket 29 is fitted into a recess between a forward-end-side surface of the flange portion 20c and the rear end of the male screw portion 20d. The gasket 29 prevents gas leakage when the gas sensor 300 is attached to the exhaust pipe.

The protector 62 is a tubular member formed of a metal (e.g., stainless steel) and covers the forward end portion of the gas sensor element 100 which projects from the forward end portion of the metallic shell 20. A rear end portion of the protector 62 is bent outward in the radial direction. This rear end portion is held between the forward-end-side surface of the flange portion 140 of the gas sensor element 100 and the step portion 20b of the metallic shell 20, whereby the protector 62 is fixed. When the metallic shell 20 and the gas sensor element 100 are combined together, the protector 62 is inserted into the metallic shell 20 from the rear end side of the metallic shell 20, and the rear end portion of the protector 62 is brought into contact with the step portion 20b of the metallic shell 20. Further, the gas sensor element 100 is inserted into the metallic shell 20 from the rear end side of the metallic shell 20, and the front end surface of the flange portion 140 is brought into contact with the rear end portion of the protector 62. The outside electrode 120 provided on the outer surface of the gas sensor element 100 is brought into contact with the protector 62 at the flange portion 140, and electrically communicates with the metallic shell 20 through the protector 62. Notably, the protector 62 has a plurality of holes for introducing exhaust gas into the interior of the protector 62. The exhaust gas having flowed into the interior of the protector 62 through the plurality of holes is supplied to the outside electrode 120 as a gas to be detected.

A powder charged portion 31 is disposed in a gap between the metallic shell 20 and the rear end of the flange portion 140 of the gas sensor element 100. The powder charged portion 31 is formed by charging a powder material containing talc powder and compressing the charged powder material. The powder charged portion 31 seals the gap between the gas sensor element 100 and the metallic shell 20. A tubular insulating member (ceramic sleeve) 32 is disposed on the rear end side of the powder charged portion 31.

The outer tube 40 is a member formed of a metallic material such as stainless steel and is joined to the rear end portion of the metallic shell 20 such that the outer tube 40 covers a rear end portion of the gas sensor element 100. A metal ring 33 formed of a metallic material such as stainless steel is disposed between the inner surface of a rear end portion of the metallic shell 20 and the outer surface of a forward end portion of the outer tube 40. The forward end portion of the outer tube 40 is crimped by the rear end portion of the metallic shell 20, whereby the metallic shell 20 and the outer tube 40 are fixed to each other. As a result of the crimping, a bent portion 20a is formed on the rear end side of the flange portion 20c. As a result of forming the bent portion 20a at the rear end portion of the metallic shell 20, the insulating member 32 is pressed toward the forward end side. As a result, the powder charged portion 31 is crushed, whereby the insulating member 32 and the powder charged portion 31 are crimp-fixed, and the gap between the gas sensor element 100 and the metallic shell 20 is sealed.

An insulating separator 34 having an approximately cylindrical shape is disposed inside the outer tube 40. The separator 34 has a passage hole 35 which penetrates the separator 34 in the direction of the axial line O and through which the lead wire 60 is passed. The lead wire 60 is electrically connected to a connection terminal 70. The connection terminal 70 is a member for taking out the sensor output to the outside and is disposed such that it comes into contact with the reference electrode 130. A grommet 36 having an approximately circular columnar shape is disposed inside the outer tube 40 such that the grommet 36 is in contact with the rear end of the separator 34. The grommet 36 has a passage hole which extends along the axial line O and through which the lead wire 60 is passed. The grommet 36 may be formed of, for example, a rubber material such as silicon rubber or fluoro rubber.

The outer tube 40 has a plurality of first vent holes 41 formed in its side wall at a position on the forward end side of the position of the grommet 36 such that the first vent holes 41 are arranged in the circumferential direction. A tubular gas-permeable filter 37 is fitted onto the radially outer side of a rear end portion of the outer tube 40 so as to cover the first vent holes 41. Further, the tubular protecting outer tube 38 formed of a metal surrounds the filter 37 from the radially outer side. The protecting outer tube 38 may be formed of, for example, stainless steel. The protecting outer tube 38 has a plurality of second vent holes 39 formed in its side wall such that the second vent holes 39 are arranged in the circumferential direction. As a result, an external gas can be introduced into the interior of the outer tube 40 through the second vent holes 39 of the protecting outer tube 38, the filter 37, and the first vent holes 41 of the outer tube 40 and then to the reference electrode 130 of the gas sensor element 100. Notably, the filter 37 is held between the outer tube 40 and the protecting outer tube 38 by crimping the outer tube 40 and the protecting outer tube 38 on the forward end and rear end sides of the second vent holes 39. The filter 37 may be formed of a porous structure of a water-repellent resin such as a fluoro resin. Since the filter 37 is water repellent, the filter 37 allows introduction of a reference gas (air) into the space inside the gas sensor element 100 while preventing passage of external water therethrough.

According to the thus-fabricated gas sensor, a gas sensor can be provided having an electrode which exhibits a room temperature conductivity of 200 S/cm or higher.

E. Experiments and Results Thereof

Hereinafter, experimental evidence that advantageous technical features of the present invention can be attained will be described based on the results of experiments. The evidence is supported by the following parameters F1 to F4:

(F1) a room temperature conductivity of 200 S/cm or higher can be attained by regulating the compositional proportions of the conductive oxide sintered body to satisfy formulas (1), and (2a) to (2d);

(F2) a conductive oxide sintered body exhibiting higher conductivity at room temperature can be produced by choosing La as the sole rare earth element RE;

(F3) a room temperature conductivity of 500 S/cm can be attained by regulating the compositional proportions to satisfy formulas (3a) to (3d); and (F4) a room temperature conductivity of 500 S/cm or higher can be attained by regulating the compositional proportions to satisfy formulas (4a) to (4d), even when deficient in a rare earth element RE (i.e., $a<(b+c+d)$).

Table 1 below shows the compositions of the conductive oxide sintered bodies and room temperature conductivity measurements. In this experiment, 26 conductive oxide sintered body samples S01 to S26 listed in Table 1 were produced, and the conductivity of each sample was measured at room temperature (25° C.). Samples S01 to S19 satisfy the aforementioned compositional relationships given by formulas (1), and (2a) to (2d), whereas samples S20 to S26, marked with "*" do not satisfy the aforementioned compositional relationships given by formulas (1), and (2a) to (2d).

TABLE 1

| Sample No. | $RE_aCu_bFe_cNi_dO_x$ | | | | Room temp. cond. σ 25° C. (S/cm) |
|---|---|---|---|---|---|
| | RE | a | b | c | d | |
| | | Element proportions (mol ratio) | | | | |
| S01 | La | 0.500 | 0.100 | 0.125 | 0.275 | 932 |
| S02 | La | 0.500 | 0.100 | 0.075 | 0.275 | 1875 |
| S03 | La | 0.500 | 0.150 | 0.025 | 0.275 | 835 |
| S04 | La | 0.500 | 0.200 | 0.250 | 0.150 | 286 |
| S05 | La | 0.500 | 0.100 | 0.200 | 0.200 | 506 |
| S06 | La | 0.500 | 0.100 | 0.100 | 0.300 | 755 |
| S07 | La | 0.500 | 0.060 | 0.165 | 0.275 | 710 |
| S08 | La | 0.500 | 0.075 | 0.150 | 0.275 | 911 |
| S09 | La | 0.500 | 0.100 | 0.150 | 0.250 | 605 |
| S10 | La | 0.474 | 0.105 | 0.132 | 0.289 | 1007 |
| S11 | La | 0.487 | 0.103 | 0.128 | 0.282 | 1254 |
| S12 | La | 0.512 | 0.098 | 0.122 | 0.268 | 766 |
| S13 | La | 0.524 | 0.095 | 0.119 | 0.262 | 508 |
| S14 | La:Pr = 1:4 | 0.500 | 0.100 | 0.125 | 0.275 | 222 |
| S15 | La:Pr = 1:4 | 0.500 | 0.100 | 0.125 | 0.275 | 202 |
| S16 | La | 0.500 | 0.100 | 0.050 | 0.350 | 864 |

TABLE 1-continued

| Sample | | $RE_aCu_bFe_cNi_dO_x$ Element proportions (mol ratio) | | | | Room temp. cond. σ |
| --- | --- | --- | --- | --- | --- | --- |
| No. | RE | a | b | c | d | 25° C. (S/cm) |
| S17 | La | 0.444 | 0.111 | 0.139 | 0.306 | 806 |
| S18 | La | 0.412 | 0.118 | 0.147 | 0.324 | 779 |
| S19 | La | 0.375 | 0.125 | 0.156 | 0.244 | 343 |
| S20* | La | 0.500 | 0.000 | 0.225 | 0.275 | 101 |
| S21* | La | 0.500 | 0.050 | 0.175 | 0.275 | 188 |
| S22* | La | 0.500 | 0.100 | 0.300 | 0.100 | 98 |
| S23* | La | 0.500 | 0.225 | 0.000 | 0.275 | 18 |
| S24* | La | 0.500 | 0.000 | 0.000 | 0.500 | 19 |
| S25* | La | 0.545 | 0.091 | 0.114 | 0.250 | 70 |
| S26* | La | 0.333 | 0.133 | 0.167 | 0.367 | 144 |

Each conductive oxide sintered body sample was produced by the production method shown in FIG. 1 and then subjected to surface polishing, to thereby prepare a rectangular parallel-piped sample (3.0 mm×3.0 mm×15.0 mm). In step T110 (FIG. 1), raw material powders were weighed and mixed so as to attain the compositions shown in Table 1. In samples S01 to S13, and S16 to S26, the rare earth element RE was La. Also, RE of sample S14 included La and Pr, and that of sample S15 included La and Nd. In the case of sample S14, raw material powders were weighed and mixed so as to attain an La/Pr mole ratio of 1:4, whereas in the case of sample S15, raw material powders were weighed and mixed so as to attain an La/Nd mole ratio of 1:4. In production of samples S10, S11, S17, S18, S19, and S26, raw material powders were weighed and mixed so that coefficients a to d satisfy a<(b+c+d). Conductivity was measured through the following procedure.

<Conductivity Measurement>

The conductivity of each sample was measured by a DC four-terminal method. The electrodes and electrode wire made of Pt were employed in the conductivity measurement. The conductivity was measured by means of a voltage/current generator (Monitor 6264, product of ADC Corporation).

Among samples S01 to S26 in Table 1, all of samples S01 to S19, satisfying compositional relationships given by formulas (1) and (2a) to (2d), exhibited a room temperature conductivity of 200 S/cm or higher. In contrast, samples S20 to S26, not satisfying compositional relationships given by formulas (1) and (2a) to (2d), exhibited a room temperature conductivity lower than that of any of samples S01 to S19.

Thus, the conductive oxide sintered bodies having compositional proportions satisfying formulas (1), and (2a) to (2d) were found to successfully exhibit a room temperature conductivity of 200 S/cm or higher. The conductive oxide sintered bodies having compositional proportions satisfying formulas (1), and (2a) to (2d), which can successfully exhibit a room temperature conductivity of 200 S/cm or higher, are suitable as conductive oxide sintered bodies for use as an electrode of a gas sensor (parameter F1).

Among samples S01 to S19 in Table 1 satisfying compositional relationships given by formulas (1) and (2a) to (2d), the samples S01 to S13, and S16 to S19 (excluding samples S14 and S15) contain La as the sole rare earth element RE. All of these samples exhibited a room temperature conductivity of 286 S/cm or higher. In contrast, among samples S01 to S19 satisfying compositional relationships given by formulas (1) and (2a) to (2d), samples S14 and S15, including a rare earth element RE other than La, exhibited a room temperature conductivity lower than that of samples S01 to S13, and that of S16 to S19 including La as the sole rare earth element RE.

Thus, conductive oxide sintered bodies satisfying compositional relationships given by formulas (1) and (2a) to (2d) and including La as the sole rare earth element RE were found to successfully exhibit a higher conductivity at room temperature, as compared with conductive oxide sintered bodies including a rare earth element RE other than La. Also, the conductive oxide sintered bodies satisfying compositional relationships given by formulas (1) and (2a) to (2d) and including La as the sole rare earth element RE are suitable as conductive oxide sintered bodies for use as an electrode of a gas sensor element (parameter F2).

Among samples S01 to S13, and S16 to S19 in Table 1, which satisfy compositional relationships given by formulas (1) and (2a) to (2d), and which include La as the sole rare earth element RE, all the samples S01 to S03, S5 to S13, and S16 to S18, further satisfying compositional relationships given by formulas (3a) to (3d), were found to exhibit a room temperature conductivity of 500 S/cm or higher.

Thus, conductive oxide sintered bodies satisfying compositional relationships given by formulas (1), and (3a) to (3d) and including La as the sole rare earth element RE were found to successfully exhibit a high conductivity at a room temperature of 500 S/cm or higher. Also, the conductive oxide sintered bodies satisfying compositional relationships given by formulas (1) and (2a) to (2d) and including La as the sole rare earth element RE are further suitably employed in a gas sensor element (parameter F3).

Among samples S01 to S26 in Table 1, samples S10, S11, S17 to S19, and S26 satisfy the conditions of coefficients a to d as a<(b+c+d). Among these samples, samples S10, S11, S17, and S18 satisfy the compositional relationships given by formulas (1), and (4a) to (4d). All of the samples S10, S11, S17, and S18 satisfying the compositional relationships given by formulas (1), and (4a) to (4d) exhibited a room temperature conductivity of 500 S/cm or higher. In contrast, sample S19 having a coefficient a falling outside the condition (4a), and sample S26 having a coefficient a falling outside the condition (2a) and a coefficient d falling outside the condition (2d) exhibited a room temperature conductivity lower than that of samples S10, S11, S17, and S18, satisfying the compositional relationships given by formulas (1), and (4a) to (4d).

Thus, conductive oxide sintered bodies satisfying compositional relationships given by formulas (1), and (4a) to (4d) were found to successfully exhibit a room temperature conductivity of 500 S/cm or higher, even when deficient in a rare earth element RE (i.e., a<(b+c+d)). Also, conductive oxide sintered bodies satisfying compositional relationships given by formulas (1), and (4a) to (4d) and including La as the sole rare earth element RE are further suitable as a conductive oxide sintered body for use in a gas sensor (parameter F4).

Table 2 below shows conductivity measurements at 900° C., B constant values, and thermal electromotive force values at 770° C. of typical samples selected from those of Table 1. B constant and thermal electromotive force were determined through the following procedure.

TABLE 2

| | | RE$_a$Cu$_b$Fe$_c$Ni$_d$O$_x$ | | | | Conductivity | | | Thermal electromotive |
|---|---|---|---|---|---|---|---|---|---|
| Sample | | Element proportions (mol ratio) | | | | 25° C. | 900° C. | B const. | force 770° C. |
| No. | RE | a | b | c | d | (S/cm) | (S/cm) | (K$^{-1}$) | (μV/K) |
| S01 | La | 0.500 | 0.100 | 0.125 | 0.275 | 932 | 461 | −281 | −16.1 |
| S02 | La | 0.500 | 0.150 | 0.075 | 0.275 | 1875 | 812 | −335 | −19.8 |
| S08 | La | 0.500 | 0.075 | 0.150 | 0.275 | 911 | 472 | −262 | −16.6 |
| S11 | La | 0.487 | 0.103 | 0.128 | 0.282 | 1254 | 634 | −273 | −17.0 |
| S20* | La | 0.500 | 0.000 | 0.225 | 0.275 | 101 | 29 | −505 | −2.2 |
| S22* | La | 0.500 | 0.100 | 0.300 | 0.100 | 98 | 151 | 175 | 24.7 |

<Measurement of B Constant>

B constant was calculated from a conductivity measurement of a sample measured at 25° C. and 900° C. by the aforementioned <Conductivity Measurement> employing the following formula (5):

$$B \text{ constant} = \ln(\rho 1/\rho 2)/(1/T1 - 1/T2) \quad (5)$$

$$\rho 1 = 1/\sigma 1$$

$$\rho 2 = 1/\sigma 2$$

ρ1: resistivity (Ωcm) at absolute temperature T1 (K)
ρ2: resistivity (Ωcm) at absolute temperature T2 (K)
σ1: conductivity (S/cm) at absolute temperature T1 (K)
σ2: conductivity (S/cm) at absolute temperature T2 (K)
T1=298.15 (K)
T2=1,173.15 (K)

<Measurement of Thermal Electromotive Force>

The thermal electromotive force was measured by a steady-state direct current method. One longitudinal end of each sample (3.0 mm×3.0 mm×15 mm) was heated, to thereby generate a difference in temperature. An R thermocouple (Pt–Pt13Rh) was attached to each end, whereby the temperature difference was read out. The voltage-temperature difference correlation between two ends was determined, and the thermal electromotive force at 770° C. was derived by a least-squares method. The above measurement was performed by means of a thermoelectric characteristic analyzer (ZEM-3, product of ULVAC Riko). The measurement was performed under He gas at low pressure.

Samples S01, S02, S08, and S11 in Table 2 which satisfy the compositional relationships given by formulas (1) and (2a) to (2d) all exhibited a conductivity at room temperature (25° C.) of 200 S/cm or higher. Also, these samples exhibited a sufficiently small B constant absolute value of 400 K$^{-1}$ or less, indicating that the samples exhibited satisfactorily high conductivity at room temperature. Even under temperature variation, the conductivity was satisfactorily high. Furthermore, samples S01, S02, S08, and S11 in Table 2 exhibited a thermal electromotive force (absolute value) at 770° C. of 21 μV/K or lower, which is sufficiently small.

The conductive oxide sintered body having such a conductivity, an absolute value of B constant, and an absolute value of thermal electromotive force at 770° C. is particularly suited for a conductive oxide sintered body for use in a gas sensor. The reason for this is as follows. Since a gas sensor element is operated at room temperature to 200° C. or higher, the room temperature conductivity is preferably high. When the absolute value of B constant of the oxide sintered body is 400 K$^{-1}$ or lower, the sintered body is suitably used as a conductor layer (an electrode of a gas sensor element). In a gas sensor, a difference in temperature of about 500° C. may be generated between two ends of an electrode. When the electrode formed from a conductive oxide sintered body has a small absolute value of thermal electromotive force at 770° C., sensing noise, which would otherwise be generated in response to the temperature difference between two ends of the electrode, can be sufficiently reduced, whereby an increase in measurement error can be suppressed.

Notably, although not given in the table, samples satisfying the aforementioned compositional relationships given by formulas (1), and (2a) to (2d) were found to exhibit almost the same B constants and thermal electromotive force values as those of samples S01, S02, S08, and S11. That is, samples S01 to S19 satisfying the aforementioned compositional relationships given by formulas (1), and (2a) to (2d) were found to have characteristics suited for providing a conductive oxide sintered body for a gas sensor.

Figure 6:
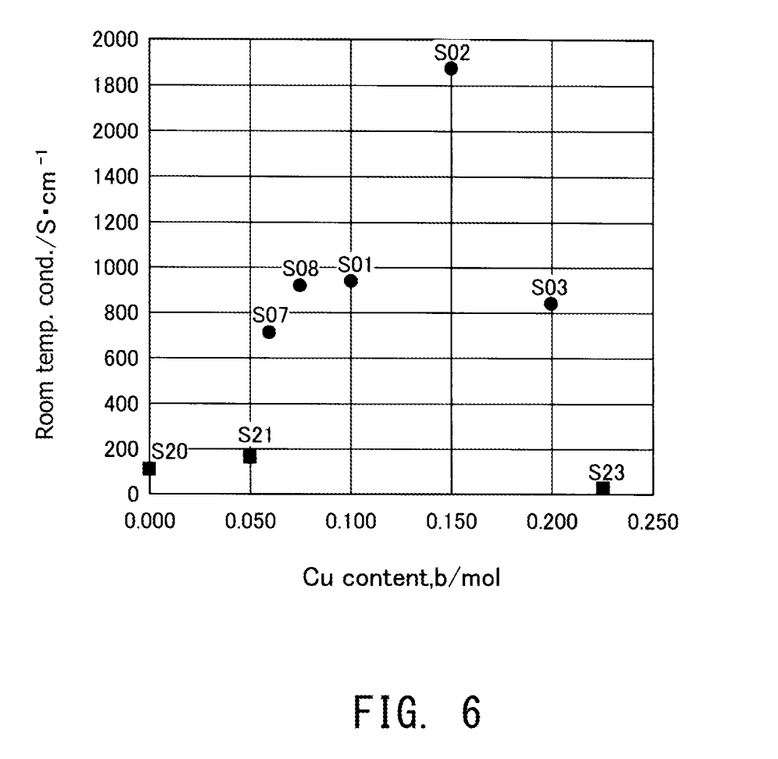
FIG. 6 is a graph showing the relationship between Cu content and room temperature conductivity.

FIG. 6 is a graph showing the relationship between Cu content and room temperature conductivity. In FIG. 6, data of typical examples selected from those listed in Table 1 are shown. Specifically, the selected samples are samples S01, S02, S03, S07, S08, S20, S21, and S23, each having an Ni coefficient d of 0.275. The variation in room temperature conductivity with respect to the Cu coefficient b is given in FIG. 6. In FIG. 6, samples satisfying the aforementioned compositional relationships given by formulas (1), and (2a) to (2d) are denoted with a black dot, whereas samples not satisfying the aforementioned compositional relationships given by formulas (1), and (2a) to (2d) are denoted with a black square. The same will be applied to FIGS. 7 and 8. As is clear from FIG. 6, when the room temperature conductivity is 200 S/cm or higher, the Cu coefficient b preferably satisfies 0.050<b≤0.200 (formula (2a)). When the room temperature conductivity is 500 S/cm or higher, the Cu coefficient b particularly preferably satisfies 0.060≤b≤0.200 (formula (3a)).

Figure 7:
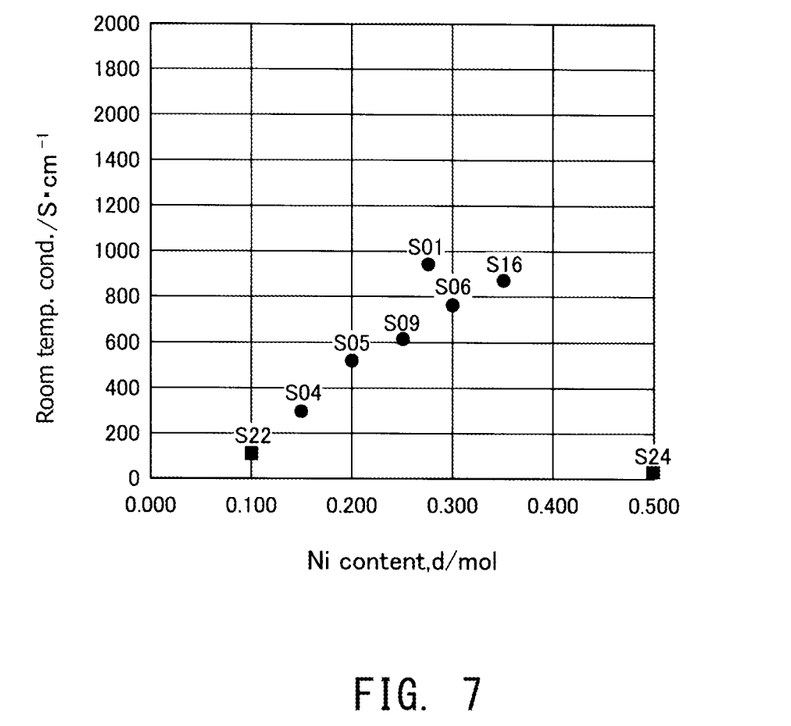
FIG. 7 is a graph showing the relationship between Ni content and room temperature conductivity.

FIG. 7 is a graph showing the relationship between Ni content and room temperature conductivity. In FIG. 7, data of typical examples selected from those listed in Table 1 are shown. Specifically, the selected samples are samples S01, S04, S05, S06, S09, and S16, each having a Cu coefficient b of 0.100 and satisfying the aforementioned compositional relationships given by formulas (1), and (2a) to (2d); sample S22, not satisfying the aforementioned compositional relationships given by formulas (1), and (2a) to (2d); and sample S24, having a Cu coefficient b of 0 and not satisfying the aforementioned compositional relationships given by formulas (1), and (2a) to (2d). The variation in room temperature conductivity with respect to the Ni coefficient d is given in FIG. 7. As is clear from FIG. 7, when the room temperature conductivity is 200 S/cm or higher, the Ni coefficient d preferably satisfies 0.150≤d≤0.350 (formula (2d)). When the room temperature conductivity is 500 S/cm or higher, the Ni coefficient d particularly preferably satisfies 0.200≤d≤0.350 (formula (3d)).

Figure 8:
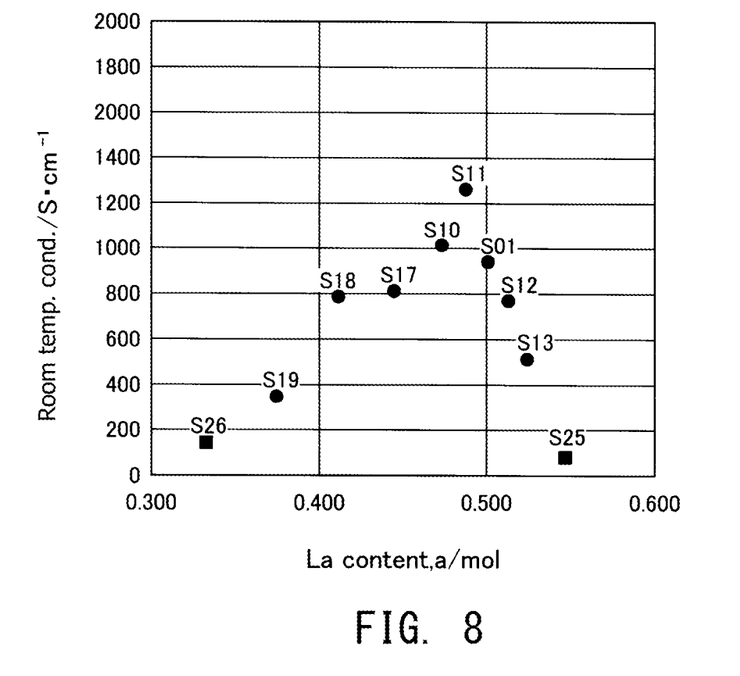
FIG. 8 is a graph showing the relationship between La content and room temperature conductivity.

FIG. 8 is a graph showing the relationship between La content and room temperature conductivity. In FIG. 8, data of typical examples selected from those listed in Table 1 are shown. Specifically, the selected samples are samples S01, S10 to S13, and S17 to S19, each having almost constant proportions among Cu coefficient (b), Fe coefficient (c), and Ni coefficient (d), and satisfying the aforementioned compositional relationships given by formulas (1), and (2a) to (2d); and samples S25 and S26, not satisfying the aforementioned compositional relationships given by formulas (1), and (2a) to (2d). The variation in room temperature conductivity with respect to the La coefficient a is given in FIG. 8. As is clear from FIG. 8, when the room temperature conductivity is 200 S/cm or higher, the La coefficient a preferably satisfies 0.375≤a≤0.524 (formula (2a)). When the room temperature conductivity is 500 S/cm or higher, the La coefficient a particularly preferably satisfies 0.412≤a≤0.524 (formula (3a)). As is also clear from FIG. 8, samples satisfying the aforementioned compositional relationships given by formulas (1), and (2a) to (2d) exhibited high conductivity at room temperature, even when the La amount was adjusted so as to deviate from the stoichiometric amount.

Hereinafter, experimental evidence that another advantageous technical feature of the present invention can be attained will be described based on the results of experiments. The evidence is supported by the following parameter F5: thermal expansion coefficient can be lowered, as compared with the case in which the amount of Cu (in terms of atom %) is equal to or higher than that of Fe, by adjusting the Cu coefficient b to be smaller than the Fe coefficient c; i.e., by adjusting the amount of Cu to be smaller than the amount of Fe.

Table 3 below shows the composition of the conductive oxide sintered bodies, the ratios of Cu amount to the sum of Cu amount and Fe amount (b/(b+c)) in the conductive oxide sintered bodies, and thermal expansion coefficient measurements, wherein the conductive oxide sintered bodies are typical samples selected from those in Table 1.

TABLE 3

| Sample No. | RE | $RE_aCu_bFe_cNi_dO_x$ Element proportions (mol ratio) | | | | | Thermal expansion coeff. ×10$^{-6}$ (K$^{-1}$) |
| --- | --- | --- | --- | --- | --- | --- | --- |
| | | a | b | c | d | b/(b + c) | |
| S01 | La | 0.500 | 0.100 | 0.125 | 0.275 | 0.444 | 13.4 |
| S02 | La | 0.500 | 0.150 | 0.075 | 0.275 | 0.667 | 13.9 |
| S03 | La | 0.500 | 0.200 | 0.025 | 0.275 | 0.889 | 13.9 |
| S04 | La | 0.500 | 0.100 | 0.250 | 0.150 | 0.286 | 12.9 |
| S05 | La | 0.500 | 0.100 | 0.200 | 0.200 | 0.333 | 13.3 |
| S06 | La | 0.500 | 0.100 | 0.100 | 0.300 | 0.500 | 13.7 |
| S21* | La | 0.500 | 0.050 | 0.175 | 0.275 | 0.222 | 12.6 |

Figure 9:
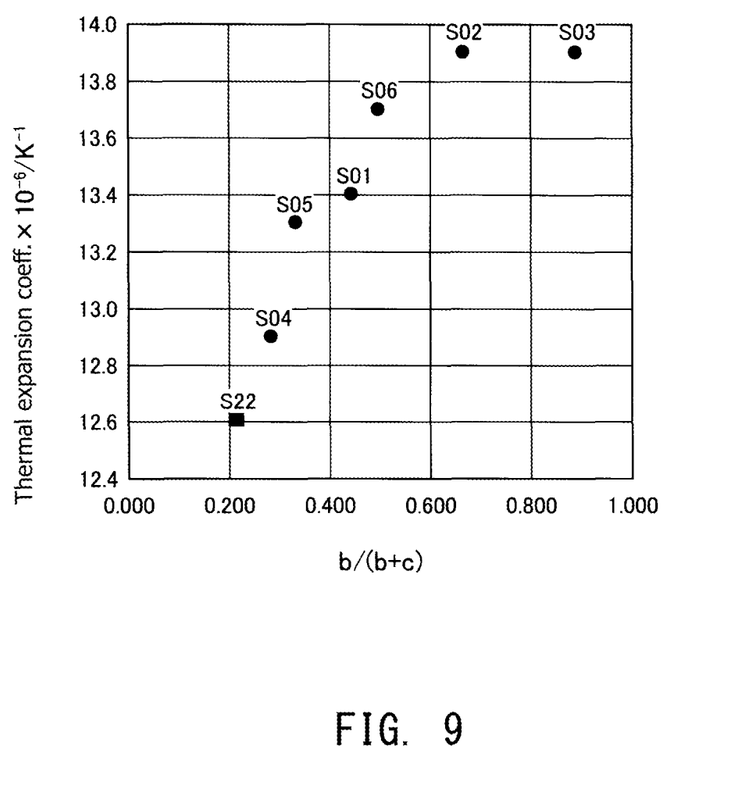
FIG. 9 is a graph showing the relationship between the ratio (b/(b+c)) and thermal expansion coefficient.

FIG. 9 is a graph showing the relationship between the ratio (b/(b+c)) and thermal expansion coefficient. The thermal expansion coefficient was determined by the following procedure.

<Thermal Expansion Coefficient Measurement>

The thermal expansion coefficient of each sample at room temperature (25° C.) to 1,000° C. was measured by means of TMA8310 (Rigaku Corporation). $Al_2O_3$ was used as a standard (reference) sample. Measurement was performed in air at a temperature elevation rate of 10.0° C./min.

Among samples S01 to S06, and S21 in Table 3, samples S01, S04, S05, and S21, having a ratio (b/(b+c)) smaller than 0.5, correspond to samples having a Cu coefficient b smaller than the Fe coefficient c; i.e., having an amount of Cu (in terms of atom %) smaller than the amount Fe. Samples S02, S03, and S06, having a ratio (b/(b+c)) of 0.5 or greater, correspond to samples having an amount of Cu equal to or greater than an amount of Fe. As is clear from Table 3, samples S01, S04, S05, and S21, having an amount of Cu smaller than the amount of Fe, exhibited a lower thermal expansion coefficient, as compared with samples S02, S03, and S06, having an amount of Cu equal to or greater than the amount of Fe. As is clear from FIG. 9, when the ratio (b/(b+c)) is smaller than 0.5, the thermal expansion coefficient is significantly lowered.

Thus, conductive oxide sintered bodies satisfying the aforementioned compositional relationships given by formulas (1), and (2a) to (2d) and having a Cu coefficient b smaller than an Fe coefficient c exhibited a lower thermal expansion coefficient, as compared with samples having a Cu coefficient b equal to or higher than an Fe coefficient c (foundation F5). Meanwhile, yttria-stabilized zirconia (YSZ), which is generally employed as a gas sensor substrate, has a thermal expansion coefficient of 10×10$^{-6}$ (K$^{-1}$), and aluminum oxide has a thermal expansion coefficient of 8×10$^{-6}$ (K$^{-1}$). Samples S01, S04, and S05, having an amount of Cu (in terms of atom %) smaller than the amount of Fe, exhibited a thermal expansion coefficient closer to that of the above substrate materials, as compared with samples S02, S03, and S06, having an amount of Cu equal to or greater than an amount of Fe. Thus, in the case where a conductive oxide sintered body is formed by applying a paste of the conductive oxide sintered body onto a substrate and secondarily firing the paste, the generation of cracks and the like, which would otherwise be caused by the difference in thermal expansion coefficient between the substrate and the conductive oxide sintered body, can be prevented. Notably, sample S21, which does not satisfy the aforementioned compositional relationships given by formulas (1), and (2a) to (2d), has an amount of Cu amount smaller than the amount of Fe, and exhibited a lower thermal expansion coefficient. However, as described with reference to Table 1, sample S21 had a room temperature conductivity of 200 S/cm or lower. Therefore, as compared with samples S01, S04, and S05, sample S21 is less suitable as a conductive oxide sintered body for a gas sensor.

F. Modifications

The present invention is not limited to the aforementioned embodiments and modifications and can be carried out in a variety of forms within the spirit and scope of the present invention. For example, technical features of embodiments and modifications which correspond to those of the technical features of the embodiments disclosed under the heading "Summary of the Invention" may be appropriately substituted or combined, for solving the entire or a part of the aforementioned problems or for attaining the entire or a part of the aforementioned effects. Also, if the technical features are not described as essential features in the specification, these may be appropriately deleted.

•Modification 1

In the aforementioned embodiment, the reference electrode 130 of the gas sensor 300 is formed of a conductive oxide sintered body, but another configuration may also be possible. In one example, the outside electrode 120 formed of a conductive oxide sintered body may be employed instead of or in addition to the reference electrode 130.

•Modification 2

In the aforementioned embodiment, the gas sensor 300 is an oxygen sensor. However, alternatively, the same conductive oxide sintered body as employed in the aforementioned embodiment may be applied to an electrode of a gas sensor (e.g., an $NO_x$ sensor) for determining the concentration of another gas.

•Modification 3

In the aforementioned embodiment, the gas sensor element 100 is configured to include the substrate 110 made of a ceramic material (solid electrolyte) having the shape of a bottomed tube, provided with a pair of electrodes 120, 130. However, another configuration may also be possible. In one example, the substrate 110 made of a ceramic material (solid electrolyte) having a plate-like shape and extending along the longitudinal direction is provided with a pair of electrodes, wherein one electrode is exposed to a measurement gas, and the other electrode is exposed to a reference gas. Similarly, the same conductive oxide sintered body as employed in the aforementioned embodiment may be applied to at least one of the electrodes.

This application is based on Japanese Patent Application No. 2016-15840 filed Aug. 12, 2016, the disclosure of which is incorporated herein by reference in its entirety.

What is claimed is:

1. A gas sensor comprising a conductive oxide sintered body, including a crystal phase having a perovskite-type oxide crystal structure represented by a compositional formula: $RE_aCu_bFe_cNi_dO_x$ wherein RE represents a rare earth element, wherein the following conditions: a+b+c+d=1, 1.25≤x≤1.75, and a<(b+c+d) are satisfied, and wherein a, b, c, and d satisfy the following conditions:

$0.412 \leq a < 0.500$;

$0.060 \leq b \leq 0.200$;

$0.025 \leq c \leq 0.200$; and $0.150 \leq d \leq 0.350$, wherein b is smaller than c.

2. A gas sensor, comprising an electrode formed of a conductive oxide sintered body, including a crystal phase having a perovskite-type oxide crystal structure represented by a compositional formula: $RE_aCu_bFe_cNi_dO_x$ wherein RE represents a rare earth element, wherein the following conditions: a+b+c+d=1, 1.25≤x≤1.75, and a<(b+c+d) are satisfied, and wherein a, b, c, and d satisfy the following conditions:

$0.412 \leq a < 0.500$;

$0.060 \leq b \leq 0.200$;

$0.025 \leq c \leq 0.200$; and $0.150 \leq d \leq 0.350$, wherein b is smaller than c.

3. The gas sensor as claimed in claim 2, which is an oxygen sensor.

4. The gas sensor as claimed in claim 3, wherein the electrode is a reference electrode.

5. The conductive oxide body as claimed in claim 1 which contains substantially no alkaline earth metal compound as an essential component.

6. The gas sensor as claimed in claim 1, wherein $0.474 \leq a < 0.5$.

7. The gas sensor as claimed in claim 2, wherein $0.474 \leq a < 0.5$.

* * * * *